(12) United States Patent
Oppenheim et al.

(10) Patent No.: US 6,531,573 B1
(45) Date of Patent: Mar. 11, 2003

(54) ANTIFUNGAL AND ANTIBACTERIAL PEPTIDES

(75) Inventors: Frank G. Oppenheim, Chestnut Hill, MA (US); Tao Xu, Newton, MA (US); F. Donald Roberts, Dover, MA (US); Peter Spacciapoli, Newbury, MA (US); Phillip M. Friden, Bedford, MA (US)

(73) Assignees: Trustees of Boston University, Watertown, MA (US); Periodontix, Inc., Boston, MA (US)

( * ) Notice: Subject to any disclaimer, the term of this patent is extended or adjusted under 35 U.S.C. 154(b) by 0 days.

(21) Appl. No.: 08/993,235

(22) Filed: Dec. 18, 1997

(51) Int. Cl.⁷ ............... A61K 38/00; A61K 38/02; C07K 5/00; C07K 7/00

(52) U.S. Cl. ............... 530/326; 530/327; 514/13; 514/14

(58) Field of Search ............... 530/326, 327; 514/13, 14

(56) References Cited

U.S. PATENT DOCUMENTS

| | | |
|---|---|---|
| 4,705,777 A | 11/1987 | Lehrer et al. ............ 514/12 |
| 4,725,576 A | 2/1988 | Pollock et al. ............ 514/2 |
| 5,032,574 A | 7/1991 | Wilde et al. ............ 514/12 |
| 5,126,257 A | 6/1992 | Gabay et al. ............ 435/212 |
| 5,221,732 A | 6/1993 | Chen et al. ............ 530/326 |
| 5,225,399 A | 7/1993 | Zasloff et al. ............ 514/13 |

(List continued on next page.)

FOREIGN PATENT DOCUMENTS

| | | |
|---|---|---|
| JP | 66-234653 | 8/1994 |
| JP | 6-287146 | 10/1994 |
| WO | 94/21672 | 9/1994 |

OTHER PUBLICATIONS

Richardson et al., "The Influence of Histatin–5 Fragments on the Mineralization of Hydroxyapatite" *Arch. Oral Biol.* 38:997–1002, 1993.

Dickinson et al., "Human Submandibular Gland Statherin and Basic Histidine–Rich Peptide and Encoded by Highly Abundant mRNA's Derived from a Common Ancestral Sequence", Biochemical and Biophysical Research Communications, 149:784–790 (1987).

Docherty and Pollock, "Inactivation of Herpes Simplex Virus Types 1 and 2 by Synthetic Histidine Peptides", Antimicrobial Agents and Chemotherapy, 31:1562–1566 (1987).

(List continued on next page.)

*Primary Examiner*—Avis M. Davenport
(74) *Attorney, Agent, or Firm*—Clark & Elbing LLP

(57) ABSTRACT

Substantially pure peptides containing between 13 and 20 amino acids, inclusive, having the amino acid sequence: R1-R2-R3-R4-R5-R6-R7-R8-R9-R10-R11-R12-R13-R14-R15-R16-R17-R18-R19-R20-R21-R22-R23, where R1 is Asp or is absent; R2 is Ser or is absent; R3 is His or is absent; R4 is Ala; R5 is Lys, Gln, Arg, or another basic amino acid; R6 is Arg, Gln, Lys, or another basic amino acid; R7 is His, Phe, Tyr, Leu, or another hydrophobic amino acid; R8 is His, Phe, Tyr, Leu, or another hydrophobic amino acid; R9 is Gly, Lys, Arg, or another basic amino acid; R10 is Tyr; R11 is Lys, His, Phe, or another hydrophobic amino acid; R12 is Arg, Gln, Lys, or another basic amino acid; R13 is Lys, Gln, Arg, another basic amino acid, or is absent; R14 is Phe or is absent; R15 is His, Phe, Tyr, Leu, another hydrophobic amino acid, or is absent; R16 is Glu or is absent; R17 is Lys or is absent; R18 is His or is absent; R19 is His or is absent; R20 is Ser or is absent; R21 is His or is absent; R22 is Arg or is absent; and R23 is Gly or is absent; and where Gln cannot simultaneously occupy positions R5, R6, R12, and R13 of the amino acid sequence, as well as pharmaceutical compositions containing these peptides and methods for treating fuingal and bacterial infections using these peptides, are disclosed.

29 Claims, 1 Drawing Sheet

Histatin 3:  Asp-Ser-His-Ala-Lys-Arg-His-His-Gly-Tyr-Lys-Arg-Lys-Phe-His-Glu-Lys-His
             1            5                    10                  15

-His-Ser-His-Arg-Gly-Tyr-Arg-Ser-Asn-Tyr-Leu-Tyr-Asp-Asn
     20                  25                  30

U.S. PATENT DOCUMENTS

| | | | |
|---|---|---|---|
| 5,239,059 A | 8/1993 | Zasloff et al. | 530/325 |
| 5,304,633 A | 4/1994 | Tomita et al. | 503/327 |
| 5,324,716 A | 6/1994 | Selested et al. | 514/14 |
| 5,486,503 A | 1/1996 | Oppenheim et al. | 514/2 |
| 5,631,228 A | 5/1997 | Oppenheim et al. | 514/12 |
| 5,646,119 A * | 7/1997 | Oppenheim et al. | 514/12 |
| 5,672,351 A | 9/1997 | Chikindas et al. | 424/401 |
| 5,696,078 A * | 12/1997 | Oppenheim et al. | 514/2 |

OTHER PUBLICATIONS

Edgerton et al., "Surface–modified poly(methyl methacrylate) enhances adsorption and retains anticandidal activities of salivary histatin 5", Journal of Biomedical Material 29:1277–1286 (1995).

Iwaki et al., "Oral Immunization with Recombinant *Streptococcus Iactis* Carrying the Streptococcus mutans Surface Protein Antigen Gene", Infect. Immun., 58:2929–2934 (Sep. 1990).

Kuramitsu and Long, "Plasmid–Mediated Transformation of Streptococcus mutans", Infect. Immun., 36:435–436 (1982).

Macrina et al., "Chimeric Streptococcal Plasmids and Their Use as Molecular Cloning Vehicles in Streptococcus sanguis (Challis)", J. Bacteriol., 143:1425–1435 (1980).

Minaguchi et al., "Genetics of Human Salivary Proteins", Journal of Dental Research, 68:2–15 (1989).

Murakami et al., "Inhibitory Effects of Synthetic Histidine–Rich Peptides on Haemagglutination by Bacteroides Gingivalis 381", Arch. Oral Biol., 35:775–777 (1990).

Nishikata et al., "Salivary Histatin as a Inhibitor of a Protease Produced by the Oral Bacterium Bacteroides ginvalis", 174:625–630 (1991).

Oppenheim et al., "Histatins, a Novel Family of Histidine–Rich Proteins in Human Paretoid Secretion", J. Biol. Chem., 263:7472–7477 (1988).

Oppenheim et al., "Isolation and Characterization of a Major Histatin From Macaque Parotid Secretion", FASEB J., 4:A2165 (Apr. 1990) (Abstract only, #2731).

Raj. P.A. et al., "Salivary Histatin 5: Dependence of Sequence, Chain Length, and Helical Confirmation for Candidacidal Activity", J Biol. Chem., 265:3898–3905 (1990).

Sabatini et al., "Tissue Distribution of RNAs for Cystatins, Histatins, Statherin, and Proline–rich Salivary Proteins in Humans and Macaques", Journal of Dental Research, 68:1138–1145 (1989).

Sabatini et al., "Histatins, A Family of Salivary Histidine–Rich Proteins, are Encoded by at Least Two LOCI (HIS1 and HIS2)", Biochemical and Biophysical Research Communications, 160:495–502 (1989).

Sabatini et al., "Tissue Distribution of RNAs for Salivary–type Proteins in Humans and Monkeys: proline–rich proteins, statherin, cystatins, and histidine–rich proteins", American Journal of Human Genetics, 43(3, Supplement):A199, Absract 0795 (1988).

Santarpia et al., "A Comparison of the Inhibition of Blastospore Viability and Germ–Tube Development in Candida albicans by Histidine Peptides and Ketoconazole", Arch. Oral. Biol., 33:567–573 (1988).

Santarpia III, et al., "Preliminary Findings for In Vivo Efficacy of Salivary Histidine–Rich Polypeptidse", J. Dent. Res., 69:173 (1990) (Abstract only, #515).

Sugiyama, et al., "Rapid Purification and Characterization of Histatins (Histidine–Rich Polypeptides) from Human Whole Saliva", Archives of Oral Biology, 35:415–419 (1990).

Svanberg et al., "Oral Implantation in Humans of Streptococcus mutans Strains with Different Degrees of Hydrophobicity", Infect. Immun., 43:817–821 (1984).

Troxler et al., "Structural Relationship Between Human Salivary Histatins", J. Dent. Res., 69:2–6 (1990).

vanderSpek et al., "Molecular Cloning of Human Submandibular Histatins", Archives of Oral Biology, 35:137–143 (1990).

vanderSpek et al., "Localization of the Genes for Histatins to Human chromosome 4q13 and Tissue Distribution of the mRNAs", American Journal of Human Genetics, 45:381–387 (1989).

Xu et al., "Structure/Function analysis of Anti–Candida Activities of Histatin 1", J. Dent. Res., 68:973 (1989) (Abstract only, #853).

Xu et al., "Anticandidal Activity of Major Human Salivary Histatins", 59:2549–2554 (1991).

Xu et al., "Primary Structure and Anticandidal Activity of the Major Histatin from Parotid Secretion of the Subhuman Primate, Macac fascicularis", J. Dent. Res., 69:1717–1723 (1990).

Xu et al., "Anti–Fungal Functional Domain of Histatin 3", J. Dent. Res., 70:497, Absract 1852, (1991).

Zuo et al., "Recombinant histatins: functional domain duplication enhances candidacidal activity", Gene, 161:87–91 (1995).

* cited by examiner

Histatin 3: Asp-Ser-His-Ala-Lys-Arg-His-His-Gly-Tyr-Lys-Arg-Lys-Phe-His-Glu-Lys-His
                 1             5           10          15

-His-Ser-His-Arg-Gly-Tyr-Arg-Ser-Asn-Tyr-Leu-Tyr-Asp-Asn 20          25          30

SEQUENCE LISTING

```
<160> NUMBER OF SEQ ID NOS: 13

<210> SEQ ID NO 1
<211> LENGTH: 32
<212> TYPE: PRT
<213> ORGANISM: Homo sapiens

<400> SEQUENCE: 1

Asp Ser His Ala Lys Arg His His Gly Tyr Lys Arg Lys Phe His Glu
1               5                   10                  15

Lys His His Ser His Arg Gly Tyr Arg Ser Asn Tyr Leu Tyr Asp Asn
            20                  25                  30

<210> SEQ ID NO 2
<211> LENGTH: 23
<212> TYPE: PRT
<213> ORGANISM: Homo sapiens

<400> SEQUENCE: 2

Asp Ser His Ala Lys Arg His His Gly Tyr Lys Arg Lys Phe His Glu
1               5                   10                  15

Lys His His Ser His Arg Gly
            20

<210> SEQ ID NO 3
<211> LENGTH: 9
<212> TYPE: PRT
<213> ORGANISM: Homo sapiens

<400> SEQUENCE: 3

Ala Lys Arg His His Gly Tyr Lys Arg
1               5

<210> SEQ ID NO 4
<211> LENGTH: 12
<212> TYPE: PRT
<213> ORGANISM: Homo sapiens

<400> SEQUENCE: 4

Ala Lys Arg Phe His Gly Tyr Lys Arg Lys Phe His
1               5                   10

<210> SEQ ID NO 5
<211> LENGTH: 12
<212> TYPE: PRT
<213> ORGANISM: Homo sapiens

<400> SEQUENCE: 5

Ala Lys Arg His Phe Gly Tyr Lys Arg Lys Phe His
```

1               5                    10

<210> SEQ ID NO 6
<211> LENGTH: 12
<212> TYPE: PRT
<213> ORGANISM: Homo sapiens

<400> SEQUENCE: 6

Ala Lys Arg His His Gly Tyr Lys Arg Lys Phe Phe
1               5                    10

<210> SEQ ID NO 7
<211> LENGTH: 12
<212> TYPE: PRT
<213> ORGANISM: Homo sapiens

<400> SEQUENCE: 7

Ala Lys Arg Phe Phe Gly Tyr Lys Arg Lys Phe His
1               5                    10

<210> SEQ ID NO 8
<211> LENGTH: 12
<212> TYPE: PRT
<213> ORGANISM: Homo sapiens

<400> SEQUENCE: 8

Ala Lys Arg Phe Phe Gly Tyr Lys Arg Lys Phe Phe
1               5                    10

<210> SEQ ID NO 9
<211> LENGTH: 12
<212> TYPE: PRT
<213> ORGANISM: Homo sapiens

<400> SEQUENCE: 9

Ala Lys Arg His His Lys Tyr Lys Arg Lys Phe His
1               5                    10

<210> SEQ ID NO 10
<211> LENGTH: 12
<212> TYPE: PRT
<213> ORGANISM: Homo sapiens

<400> SEQUENCE: 10

Ala Lys Arg His His Gly Tyr His Arg Lys Phe His
1               5                    10

<210> SEQ ID NO 11
<211> LENGTH: 12
<212> TYPE: PRT
<213> ORGANISM: Homo sapiens

<400> SEQUENCE: 11

Ala Lys Arg His His Lys Tyr His Arg Lys Phe His
1               5                    10

<210> SEQ ID NO 12
<211> LENGTH: 12
<212> TYPE: PRT
<213> ORGANISM: Homo sapiens

<400> SEQUENCE: 12

Ala Lys Arg His His Gly Tyr Phe Arg Lys Phe His
1               5                    10

```
<210> SEQ ID NO 13
<211> LENGTH: 12
<212> TYPE: PRT
<213> ORGANISM: Homo sapiens

<400> SEQUENCE: 13

Ala Lys Arg Tyr Tyr Gly Tyr Lys Arg Lys Phe Tyr
 1               5                  10
```

ANTIFUNGAL AND ANTIBACTERIAL PEPTIDES

STATEMENT AS TO FEDERALLY SPONSORED RESEARCH

The invention described herein was supported in whole or in part by Grant No. DE07652 from the National Institutes of Health, which have certain rights in the invention.

BACKGROUND OF THE INVENTION

The invention relates to antifingal and antibacterial peptides.

Bacterial and fungal infections are prevalent and, in some cases, life-threatening conditions that affect otherwise healthy patients. Bacterial and fungal infections are especially dangerous for immuno-compromised patients. For these patients, systemic fungal infections can lead to death, since there are few safe and effective antifungal pharmaceuticals for intravenous use. Similarly, infections with various bacterial species can cause sever disease states and even death.

Although several antifungal agents (e.g., clotrimazole, miconazole, ketoconazole, and nystatin) and antibacterial agents (e.g., penicillin, streptomycin, tetracycline, and chlorhexidine) are currently available, these agents are not completely effective. These agents can also lead to drug resistant organisms and can produce adverse side effects. In addition, many are not appropriate for oral or systemic administration.

SUMMARY OF THE INVENTION

The invention features substantially pure peptides containing between 13 and 20 amino acids, inclusive; the peptides have the amino acid sequence: R1-R2-R3-R4-R5-R6-R7-R8-R9-R10-R11-R12-R13-R14-R15-R16-R17-R18-R19-R20-R21-R22-R23, where R1 is Asp or is absent; R2 is Ser or is absent; R3 is His or is absent; R4 is Ala; R5 is Lys, Gln, Arg, or another basic amino acid; R6 is Arg, Gln, Lys, or another basic amino acid; R7 is His, Phe, Tyr, Leu, or another hydrophobic amino acid; R8 is His, Phe, Tyr, Leu, or another hydrophobic amino acid; R9 is Gly, Lys, Arg, or another basic amino acid; R10 is Tyr; R11 is Lys, His, Phe, or another hydrophobic amino acid; R12 is Arg, Gln, Lys, or another basic amino acid; R13 is Lys, Gln, Arg, another basic amino acid, or is absent; R14 is Phe or is absent; R15 is His, Phe, Tyr, Leu, another hydrophobic amino acid, or is absent; R16 is Glu or is absent; R17 is Lys or is absent; R18 is His or is absent; R19 is His or is absent; R20 is Ser or is absent; R21 is His or is absent; R22 is Arg or is absent; and R23 is Gly or is absent; where Gln cannot simultaneously occupy positions R5, R6, R12, and R13 of the amino acid sequence of a peptide.

In preferred peptides, at least one of R7, R8, R11, and R15 is Phe; R9 is Lys; R11 is His; or at least one of R7, R8, and R15 is Tyr; or any combination of these substitutions is present in the peptide. In other preferred peptides, R1, R2, and R3 are absent; alternatively, R22 and R23 are absent; R20, R21, R22, and R23 are absent; or R18, R19, R20, R21, R22, and R23 are absent.

The peptides may have substituents bonded to either terminus of the peptide. For example, the peptide may have an acetyl or a carbamyl addition at the N-terminus, and/or an amide addition at the C-terminus.

Preferred peptides contain 13–16 amino acids, and more preferably contain 13–14 amino acids. The invention further features pharmaceutical compositions including the peptides of the invention.

The peptides of the present invention have potent antibacterial and antifungal properties, and the invention also features methods for treating bacterial and fungal infections using these peptides.

Other features and advantages of the invention will be apparent from the following description and from the claims.

BRIEF DESCRIPTION OF THE DRAWINGS

FIG. 1 shows the amino acid sequence of histatin 3.

DETAILED DESCRIPTION OF THE INVENTION

The invention features peptides containing 13 to 20 amino acids; these peptides include defined portions of the amino acid sequence of the naturally occurring protein histatin 3 (SEQ ID NO: 1), which is shown in FIG. 1. In addition, the peptides of the invention include defined portions of the amino acid sequence of histatin 3, with amino acid substitutions at particular positions of the peptides. These peptides are referred to herein as "histatin-based peptides."

Histatins (also referred to in the literature as histidine-rich proteins or HRPs) are salivary proteins that are synthesized in the parotid and submandibular-sublingual secretory glands of humans and Old World monkeys and are believed to be part of the extraimmunologic defense system of the oral cavity. The family of naturally occurring human histatins is a group of twelve low molecular weight peptides. The major family members, which make up 70–80% of the whole family, are histatins 1, 3, and 5, containing 38, 32, and 24 amino acid residues, respectively.

Preparation of the Peptides

The peptides of the present invention can thus be obtained from naturally occurring sources of histatin; alternatively, they can be obtained by recombinant DNA techniques as expression products from cellular sources. The peptides can also be chemically synthesized.

For example, cloned DNA encoding the histatins may be obtained as described by L. M. Sabatini et al., *Biochem. Biophys. Res. Comm.* 160: 495–502 (1989) and J. C. Vanderspek et al., *Arch. Oral Biol.* 35(2): 137–43 (1990). cDNA encoding the histatin-based peptides can be cloned by recombinant DNA techniques, for instance, by using degenerate oligonucleotides based on the amino acid sequence of histatin-based peptides as primers for polymerase chain reaction amplification.

Alternatively, oligonucleotides encoding histatins or histatin-based peptides can be synthesized chemically using commercially available equipment. They can then be made double-stranded and cloned into vectors for amplification in prokaryotic or eukaryotic host cells.

Histatin-based peptides can be produced in a variety of expression vector/host systems, which are available commercially or can be reproduced according to recombinant DNA and cell culture techniques. The vector/host expression systems can be prokaryotic or eukaryotic, and can include bacterial, yeast, insect, mammalian, and viral expression systems. The construction of expression vectors encoding histatin-based peptides, transfer of the vectors into various host cells, and production of peptides from transformed host cells can be accomplished using genetic engineering techniques, as described in manuals such as J. Sambrook et al., *Molecular Cloning* (2d ed. 1989) and *Current Protocols in Molecular Biology*, (F. M. Ausubel et al., eds.).

Modified histatin-based peptides can also be produced from cloned DNAs containing mutated nucleotide sequences. Histatin-based peptides encoded by expression vectors may be modified due to post-translational processing in a particular expression vector/host cell system.

These peptides can be altered by minor chemical modifications, such as by adding small substituents or by modifying one or more of the covalent bonds within or between the amino acid residues. The substituent groups can be bulky and may include one or more natural or modified amino acids. Useful modifications include the addition of a substituent to either the amino terminus, the carboxyl terminus, or to both ends of the peptide. A combination of additions at both termini is especially useful. Particularly useful modifications include acetylation or carbamylation of the amino terminus of the peptide, or amidation of the carboxyl terminus of the peptide. These alterations do not significantly diminish the antifungal or antibacterial activities of the peptides and appear to stabilize the peptide in its active form and to aid in the prevention of enzymatic degradation of these peptides.

Antifungal and Antibacterial Activities of Histatin-Based Peptides

The antifungal activity of the naturally-occurring histatins, as well as their inhibitory effect on several oral bacteria (such as the cariogenic *Streptococcus mutans* and the periodontal pathogen *Porphyromonas gingivalis*), have been demonstrated in vitro. In addition, the observation that polyhistidine peptides inactivate the herpes simplex virus in vitro and that whole saliva contains inhibitors of the human immunodeficiency virus suggests the possibility that histatins may have anti-viral activity. These in vitro studies support the potential clinical use of compositions containing histatin-based peptides for the treatment of local and systemic candidal infection, oral bacterial diseases such as caries and periodontal disease, systemic bacterial infection, and viral infection.

The antifungal activities of the histatin-based peptides can be measured in assays for killing *Candida albicans* blastoconidia (as described in T. Xu et al., *Infect. Immun.* 59(8): 2549–2554 (1991)). The antibacterial activities of the histatin-based peptides can be measured in assays for inhibition of *P. gingivalis* growth. Histatin-based peptides can also interfere with bacterial virulence by inhibiting hemagglutination caused by *B. forsythus* and *P. gingivalis* and by inhibiting proteases such as clostripain; assays that measure these inhibitory activities are therefore useful in measuring the antibacterial activities of histatin-based peptides as well.

The antifungal and antibacterial properties of the histatin-based peptides are a function of both the size and the amino acid sequence of the respective peptides. Peptides having amino acid sequences shorter than those of the naturally-occurring histatins can have antibacterial and antifingal properties that are superior to those of the naturally-occurring histatins, particularly when these properties are measured on a weight basis.

Some of the peptides of the present invention include part of the amino acid sequence:

Alternatively, the peptides of the present invention can include portions of this sequence with amino acid substitutions at one or more positions. Preferred peptides include those in which the glycine at position 9 is replaced by lysine, arginine, or another basic amino acid; the lysine at position 11 is replaced by histidine, phenylalanine or another hydrophobic amino acid; one or more of the histidines at positions 7, 8, and 15 is replaced by phenylalanine, tyrosine, leucine, or another hydrophobic amino acid; one or both of the lysines at positions 5 and 13 is replaced by arginine or another basic amino acid; or one or both of the arginines at positions 6 and 12 is replaced by lysine or another basic amino acid. Combinations of these amino acid replacements can be used as well.

The amino acid substitutions result in peptides that display enhanced antifungal activity in comparison to peptides including the native sequence. For example, the replacement of histidine at positions 7, 8, or 15 with phenylalanine, either singly or in combination, results in peptides with increased antifungal activities in comparison to peptides including the native sequence. Likewise, the replacement of the glycine at position 9 with lysine, or the lysine at position 11 with histidine or phenylalanine, either singly or in combination, results in peptides with noticeably increased fungicidal activities in comparison to peptides having the native sequence. Acetylation or carbamylation of the N-terminus of the native sequence also yields peptides with significant antifungal activity.

An additional feature of the directed amino acid substitutions of the native sequence is that particular types of amino acid substitutions result in peptides with enhanced activities, e.g. antifungal, at non-neutral pH's. For example, the substitution of histidine at positions 7, 8, and 15 with phenylalanine results in peptides having significant antifungal activity at pH 4.0. Peptides with the native sequence are essentially devoid of antifungal activity at this lower pH.

At least some of the antifungal and antibacterial properties of the histatin-based peptides of the invention appear to reside in the amino acid sequence Ala-Lys-Arg-His-His-Gly-Tyr-Lys-Arg (SEQ ID NO:3). Peptide's containing this sequence, as well as peptides having one or more amino acids substituted at various positions of this sequence, are potent antifungal and antibacterial agents. Preferred peptides include those containing the amino acid sequences:

Ala-Lys-Arg-Phe-His-Gly-Tyr-Lys-Arg-Lys-Phe-His (SEQ ID NO:4);

Ala-Lys-Arg-His-Phe-Gly-Tyr-Lys-Arg-Lys-Phe-His (SEQ ID NO:5);

Ala-Lys-Arg-His-His-Gly-Tyr-Lys-Arg-Lys-Phe-Phe (SEQ ID NO:6);

Ala-Lys-Arg-Phe-Phe-Gly-Tyr-Lys-Arg-Lys-Phe-His (SEQ ID NO:7);

Ala-Lys-Arg-Phe-Phe-Gly-Tyr-Lys-Arg-Lys-Phe-Phe (SEQ ID NO:8);

Ala-Lys-Arg-His-His-Lys-Tyr-Lys-Arg-Lys-Phe-His (SEQ ID NO:9);

Ala-Lys-Arg-His-His-Gly-Tyr-His-Arg-Lys-Phe-His (SEQ ID NO:10);

```
Asp-Ser-His-Ala-Lys-Arg-His-His-Gly-Tyr-Lys-Arg-Lys-Phe-His-Glu-Lys
 1   2   3   4   5   6   7   8   9  10  11  12  13  14  15  16  17

His-His-Ser-His-Arg-Gly (SEQ ID NO:2).
 18  19  20  21  22  23
```

Ala-Lys-Arg-His-His-Lys-Tyr-His-Arg-Lys-Phe-His (SEQ ID NO:11);

Ala-Lys-Arg-His-His-Gly-Tyr-Phe-Arg-Lys-Phe-His (SEQ ID NO:12); and

Ala-Lys-Arg-Tyr-Tyr-Gly-Tyr-Lys-Arg-Lys-Phe-Tyr (SEQ ID NO:13).

Combinations of two or more of these peptides are also effective as antifungal or antibacterial agents.

Therapeutic Applications

The peptides of the present invention can be used in pharmaceutical compositions to treat fungal infections, in particular candidal infection, as well as bacterial infections (e.g., *S. mutans, P. aeruginosa* or *P. gingivalis* infections) and viral infections (e.g., the herpes simplex virus or human immunodeficiency virus type 1 infections). Vaginal, urethral, mucosal, respiratory, skin, ear, oral, or ophthalmic fungal or bacterial infections are particularly susceptible to histatin-based peptide therapy. Microbes which are specifically amenable to histatin-based peptide therapy include:

a) *Candida albicans;*
b) *Actinomyces actinomycetemcomitans;*
c) *Actinomyces viscosus;*
d) *Bacteriodesforsythus;*
e) *Bacteriodesfragilis;*
f) *Bacteriodes gracilis;*
g) *Bacteriodes ureolyticus;*
h) *Campylobacter concisus;*
i) *Campylobacter rectus;*
j) *Campylobacter showae;*
k) *Campylobacter sputorum;*
l) *Capnocytophaga gingivalis;*
m) *Capnocytophaga ochracea;*
n) *Capnocytophaga sputigena;*
o) *Clostridium histolyticum;*
p) *Eikenella corrodens;*
q) *Eubacterium nodatum;*
r) *Fusobacterium nucleatum;*
s) *Fusobacterium periodonticum;*
t) *Peptostreptococcus micros;*
u) *Porphyromonas endodontalis;*
v) *Porphyromonas gingivalis;*
w) *Prevotella intermedia;*
x) *Prevotella nigrescens;*
y) *Propionibacterium acnes;*
z) *Pseudomonas aeruginosa;*
aa) *Selenomonas noxia;*
bb) *Staphylococcus aureus;*
cc) *Streptococcus constellatus;*
dd) *Streptococcus gordonii;*
ee) *Streptococcus intermedius;*
ff) *Streptococcus mutans;*
gg) *Streptococcus oralis;*
hh) *Streptococcus pneumonia;*
ii) *Streptococcus sanguis;*
kk) *Treponema denticola;*
ll) *Treponema pectinovorum;*
mm) *Treponema socranskii;*
nn) *Veillonellaparvula;* and
oo) *Wolinella succinogenes.*

Carriers appropriate for administration of pharmaceutical agents to the vagina, the urethra, the ear, the oral cavity, the respiratory system, the ophthalmic region, various mucosal regions, and the skin are known and described, for instance, in Pollock et al., U.S. Pat. No. 4,725,576. Compositions for treatment of systemic infection can be administered by various routes, such as intravenously or subdermally.

Compositions containing the peptides of the present invention can be used in preventive treatment as well. The complositions may contain combinations of histatin-based peptides, in order to obtain maximum activity against all developmental forms of a fungus or bacterium. The ionic strength, presence of various mono- and divalent ions, and pH of the compositions may be adjusted to obtain maximum antifungal or antibacterial activity of the histatin-based peptides, as described in T. Xu et al., *Infect. Immun.* 59(8): 2549–54 (1991).

In addition, expression vectors encoding the above-mentioned peptides can be used in antifungal or antibacterial treatments. Expression vectors may be administered in compositions which introduce genetic material encoding histatin-based peptides into cells of the patients. For example, recombinant expression vectors based on retroviruses or adenovirus vaccines may be used to infect patients.

The above-described expression vectors can also be used in bacterial substitution therapy. Bacterial substitution therapy can be used to treat fungal or bacterial infection of areas in the urinary/reproductive, respiratory and/or gastrointestinal tracts of a patient. The therapy includes: (1) transforming a particular bacterium with DNA including an expression vector which encodes a histatin-based peptide described above, thereby producing transformed cells; (2) selecting transformed cells which express the peptide encoded by the expression vector, thereby obtaining transformed cells which express a histatin-based peptide; and (3) administering transformed cells which express a histatin-based peptide in an appropriate carrier to the infected area.

Another application of bacterial substitution therapy is treatment of fungal or bacterial infections of the oral cavity. A number of species of the oral bacteria Streptococcus can be used as vehicles for the expression vectors. For example, recombinant S. lactis has been used in oral immunization of mice against a heterologous antigen. Other oral bacteria which can be used as vehicles for expression vectors, plasmids for constructing expression vectors capable of amplification in oral bacterial host cells, transformation methods, and administration of compositions containing oral bacteria to humans have been described.

The pharmaceutical compositions used in the treatment of fungal, bacterial, or viral infections discussed above are not limited to use in humans, but can have veterinary applications as well.

Hemagglutination Activity of Bacteria and Histatin Inhibition of this Activity

Even though the association between hemagglutination activity and adherence on host cells in the oral environment is not clear, it is generally accepted that hemagglutination activity is an indicator for the colonizing ability of bacteria. Periodontal pathogens must adhere to other bacteria and host cells in order to express their noxious destructive potential upon periodontal tissues. Hemagglutination is thought to be involved in bacterial colonization.

Ability for adherence on erythrocytes is of great importance in the interactions of periodontal pathogens with the host. The close proximity of these bacteria with the host tissues as well as with erythrocytes that bathe the periodontal pocket during progression of the disease, indicates multiple interrelations between these elements. Additionally, periodontal microbes require heme-containing products for their survival and multiplication; this need dictates interactions with cells such as erythrocytes that are rich in these compounds. *P. gingivalis* has been shown to possess both hemagglutinins and hemolysin that provide attachment on erythrocytes and utilization of heme-compounds.

It has been shown that histatin 5 and histatin 8 inhibit hemagglutination of *P. gingivalis* 381. Complete hemagglutination inhibition was reported for histatin 5 at a concentration of 5 nmol/ml. Thus it appears that histatins and histatin-based peptides can play a role in inhibiting bacterial growth and deleterious activity in the periodontal region.

Clostripain Inhibition by Histatin-Based Peptides

Clostripain is an endopeptidase enzyme synthesized by *Clostridium histolyticum*. This enzyme, with its protein degradative activity, can be inhibited by histatin 5 and by histatin-based peptides. Thus, histatin-based peptides can inhibit bacterial function by inhibiting bacterial enzymes which are essential for bacterial viability.

OTHER EMBODIMENTS

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

Without further elaboration, it is believed that one skilled in the art can, based on the description herein, utilize the present invention to its fullest extent.

The following specific examples are, therefore, to be construed merely as illustrative, and do not limit the remainder of the disclosure in any way hatsoever. Publications mentioned herein are hereby incorporated by reference.

EXAMPLE 1

MATERIALS AND METHODS

A. Isolation and Chemical Synthesis of Histatin-Based Peptides

The isolation and amino acid sequence determination of human histatins are performed as described in F. G. Oppenheim et al., *J. Biol. Chem.* 263(16): 7472–7477 (1988). Human parotid secretion from healthy adults is stimulated using sour lemon candies, collected with Curby cups in ice-chilled graduated cylinders, pooled, dialyzed and lyophilized. The total protein in the human parotid secretion is subjected to fractionation on Bio-Gel P-2 (Bio-Rad Laboratories, Richmond, Calif.) developed in 0.05 M ammonium formate buffer, pH 4.0. The protein fractionation enriched with histatins is further purified using reverse-phase high-performance liquid chromatography on a $C_{18}$ column. Purified histatins are evaporated to dryness, dissolved in deionized water, quantified by amino acid analysis, lyophilized, and stored at −20° C. until use.

Histatin-based peptides are synthesized by the solid phase method of B. Merrifield, *Science* 232:341–47 (1986). Peptides are synthesized by a MilliGen/Bioresearch Sam-Two Peptide Synthesizer using Fmoc L-amino acid kits (Millipore, Bedford, MA) and purified on a TSK ODS-i2OT $C_{18}$ column (5 μm, 4.6×250 nm) using RP-HPLC (Pharmacia-LKB). The purified peptides are quantified by amino acid analysis on a Beckman System 6300 amino acid analyzer.

B. *C. albincans* Killing

1) *C. albincans* Stock

A well-described strain of *C. albicans* (strain ATCC 44505, which was originally isolated from the human oral cavity) is used in the bioassay. Cultures are stored at 4° C. on Sabourand dextrose agar plates (Difco Laboratories, Detroit, Mich.) until use. Stationary phase growth cells are obtained following growth at 30° C. for 18 hours on Sabourand dextrose agar plates. Colonies are harvested and suspended in 10 mM potassium phosphate buffer (PPB), pH 7.4.

To initiate log phase growth, an aliquot of stock *C. albicans* is suspended in Sabourand dextrose broth (Difco) and incubated at 30° C. in a shaking water bath. The growth phase is determined by taking aliquots of the culture at one hour intervals to monitor the optical density (O.D.) at 560 nm. Early log phase is obtained at 4 to 6 hours, indicated by an O.D. of about 0.6. Log phase cells are harvested and utilized in the blastoconidia killing assay in a manner identical to that described for stationary phase cells. A final concentration of $10^5$ cells/ml (either stationary or log phase fungus) is used in all assays.

(2) Suspension Buffers

The standard suspension buffer utilized in the blastopore killing assay is 0.01 M PPB, pH 7.4. An alternate suspension buffer, N-2-hydroxyethylpiperazine-N'-2-ethanesulfonic acid (HEPES; Sigma Chemical Co., St. Louis, Mo.), pH 7.4, can also be utilized.

(3) Bioassays

The following assay is used to evaluate the effects of histatins on the killing of blastoconidia of *C. albicans*.

a. For the killing of blastoconidia assay, 50 μl aliquots of cells ($2 \times 10^5$ cells/ml) diluted in suspension buffer are allowed to attach to a polystyrene 96-well micro-titer plate (COSTAR, Cambridge, Mass.) for 15 minutes at room temperature, and then incubated with an equal volume of a histatin peptide in suspension buffer for 1 hour at 37° C. Controls are carried out in the absence of histatin peptide. After incubation, wells are washed three times by centrifugation at 1,000×g for 5 minutes and covered with aliquots of molten Sabourand dextrose broth (Difco) containing 2% agarose (Sigma) at 45° C. The plate is then incubated at 30° C. for 8 hours. Under such conditions, live cells will divide and begin to form colonies, while dead cells will remain as single cells. To determine the percentage of blastoconidia killed, a total of 100 single cells and/or colonies are counted under a Nikon inverted microscope at 400× magnification. The extent of killing is calculated using the formula: [1−(number of colonies in treated sample)/(number of colonies in control)]×100%.

(4) Statistical Analysis

Data are obtained by calculating the mean and standard deviation from triplicate assays. From the dose response relationship, doses effecting a 50% killing ($LD_{50}$) are determined.

C. Bacterial Growth Inhibition and Cell Killing Assays (1) Bacterial Strains and Culture Conditions a. The bacteria that is used in one investigation, Porphyromonas gingivalis strain A7A1-28, is a typical key pathogenic organism associated with destructive periodontal diseases. The bacteria are multiply subcultured in Enriched Todd Hewitt broth (ETHB, Difco Lab., Detroit, Mich.). Microorganisms are stored in the same broths containing 20% and 50% glycerol, at −20° C. and −70° C., respectively. These serve as stock cultures from which all preparations originate.

Working stock cultures are maintained by weekly transfer to Brain Heart Infusion Anaerobic Sheep Blood Agar plates (BHIA, Becton Dickinson and Co., Cockeysville, Md.), and Trypticase Soy Anaerobic Sheep Blood Agar plates (TSA, Becton Dickinson and Co., Cockeysville, Md.). Plates are incubated for 3 to 4 days under strictly anaerobic conditions. For the bacteriostatic assay, bacteria are collected from plates, inoculated into the aforementioned broth and grown at 37° C. under strictly anaerobic conditions for 24 to 48 hours.

b. Two other bacterial species are used in a bacterial cell killing assay system. These bacterial species are *Streptococcus mutans* strain SJ32 and Pseudomonas aeruginosa ATCC Accession No. 27853. The assays are performed using liquid overnight cultures (nutrient broth for *P. aeruginosa*; Todd Hewitt broth for *S. mutans*) of growth media from frozen stocks of these bacterial species. In the assay, the bacteria are diluted into assay buffer (10 mM Potassium Phosphate, pH 6.0 with 20 mM NaCl for *P. aeruginosa*; and 10 mM Potassium Phosphate, pH 5.2 with 20 mM NaCl for *S. mutans*) to a concentration of $2 \times 10^5$ cfu/ml ($1 \times 10^9$ cfu/OD/ml) and combined with an equal volume (250 μl) of peptide to produce 500 μl of incubation mixture with a final concentration of $10^5$ cfu/ml. Controls constitute buffer and bacteria but no peptide. After incubation at 37° C. (30 minutes incubation for *P. aeruginosa*; and 60 minutes incubation for *S. mutans*), the mixtures are plated onto agar media (nutrient agar for *P. aeruginosa*; and Todd Hewitt media with 0.5% glucose for *S. mutans*) and incubated at 37° C. until colonies develop. The mean number of colonies is determined from a minimum of 4 plates, and percent killing is determined by comparing the colony number arising from control cultures versus the colony number arising from peptide-containing assay mixtures.

(2) Microdilution Bacteriostatic Assay

A modification of the typical microdilution assay for the determination of minimal inhibitory concentration (MIC) of antimicrobial agents is utilized to investigate the bacteriostatic activity of the peptides. A standardized bacterial inoculum (*P. gingivalis*) is exposed to serially diluted antimicrobial peptides in an enriched broth medium that is suitable for the growth of anaerobic bacteria. The test is adapted for use in the 96-well microtiter plates. Results with the microdilution method have been shown to be comparable to other known techniques for antimicrobial susceptibility such as the dilution method, the agar dilution method, and the broth-disk elution method. In the typical assay, the microtiter plate is observed at multiple time points after inoculation for visible growth. The modification introduced here is based on the spectrophotometric reading of the microtiter plate after incubation.

Microorganisms from cultures maintained in the aforementioned plates are inoculated into 5 ml of the above-mentioned broths and cultured overnight at 37° C. under strictly anaerobic conditions with continuous agitation on a minishaker (IKA-Labortechnik, Staufen i. Br., Germany). The bacteria are grown until reaching the late log phase and are then suspended in the same broths to an optical density (O.D.) of 0.1 at 560 μm. The peptides are diluted in 0.01 M phosphate buffered saline (PBS), pH 7. Forty-μl aliquots of peptide dilutions are added to each well of a U-bottom microtiter plate (Costar, Cambridge, Mass.) to give final concentrations of 2000, 1000, 500, and 250 μM. Twenty μl of bacterial inoculum are added to all the wells. Finally, 100 μl of the suitable broth are added to each well. The optical density of the wells of the microtiter plate is determined using a microplate reader set at 550 nm, and the plate is then incubated under strictly anaerobic conditions for 24 hours. Controls are made by replacing the peptide dilutions with PBS alone. After the incubation, the mixtures in each well are mixed manually to resuspend sedimented bacteria, and the plate is then read again. The experiments are conducted twice every time. The biologic activity is calculated according to the formula:

$$100-[[(\text{Fin ODexp-In ODexp})/(\text{Fin ODctr-In ODctr})] \times 100]$$

where:

Fin ODexp is the OD of the final experimental group;

In ODexp is the OD of the initial experimental group;

Fin ODctr is the OD of the final control group; and

In ODctr is the OD of the initial control group.

In addition, the % increase in time to reach mid-log phase growth is calculated.

D. Inhibition of Hemagglutination Assays (1) Strains and Growth Conditions for Hemagglutination Assays The *P. gingivalis* strain of Section C. (1) is also used for the hemagglutination assays. The bacterial growth and culture conditions are also the same as those described in Section C. (1).

(2) Hemagglutination Assay

A classic assay is utilized to determine the hemagglufination potential of the *P. gingivalis* strain. Microorganisms are inoculated into BFB broth and cultured overnight, for approximately 24 hours at 37° C. under strictly anaerobic conditions with continuous agitation on a minishaker (IKA-Labortechnik, Staufen i. Br., Germany). The bacteria are harvested by centrifugation at 3,000 r.p.m. for 20 minutes, at 4° C., washed twice in 0.01 M phosphate buffered saline (PBS), pH 7.4, and suspended in the same buffer to an optical density of 1.0 at 550 nm. Erythrocytes are obtained from a young male with O-type blood. (No difference in hemagglutination is observed in experiments with different ABO blood groups.) One ml of blood is drawn each time, washed twice in PBS at 1,000 r.p.m. for 10 minutes at 4° C. and suspended in the same buffer at a 2% (v/v) final concentration. Fifty μl of the bacterial suspension are serially diluted in PBS (two-fold steps) in a 96-well U-bottom microplate (Costar, Cambridge, Mass.). Fifty μl of the erythrocyte suspension are added to each well. Controls without bacteria or erythrocytes are included. The microplate is slightly shaken and incubated at room temperature for 2 hours. Visible examination on a white background is used to determine hemagglutination. The amount of hemagglutination is rated as none moderate (+/−), or strong (+). Erythrocytes in control wells with PBS precipitate to the center of the well, whereas erythrocyte-bacteria aggregates precipitate at the periphery of the bottom. The hemagglutination titer is expressed as the reciprocal of the highest dilution of the bacterial suspension providing visible hemagglutination.

(3) Histatin Peptide Inhibition of Hemagglutination Assay

Preparation of erythrocyte and bacterial suspensions are the same as for the hemagglutination assay. Fifty μl of histatin peptide solutions are diluted in PBS in a U-bottom microplate, at various two-fold concentrations with 600 nmol/ml being the highest. The bacterial concentration utilized is normally twice the minimal concentration which gives strong hemagglutination. Equal volumes of the bacterial suspension are poured into the wells containing the histatin peptides. Finally, 50 μl of erythrocyte suspension are added in each well.

The microplate is slightly shaken and incubated at room temperature for 2 hours. Controls are made by replacement of the peptide dilutions with PBS only. The experiments are conducted at least twice. The lowest histatin peptide concentration without hemagglutination is determined upon visual examination. The highest final histatin peptide concentration utilized is 100 nmol/ml.

E. Clostripain Assays

Clostripain from Clostridium histolyticum (Sigma Chemical Corp., St. Louis, Mo.) is dissolved in deionized water to a concentration of 1 mg/ml (300 units/mg) and activated with the addition of 10 mmol/L DTT. To measure its hydrolytic activity, clostripain (6 units) is added to 50 nmol/L Hepes buffer, pH 7.5, containing 80 μmol/L BAPNA (benzoyl-arginine-p-nitroanilide), together with 5.6 μmol/L of histatin peptide inhibitor. As controls, assays are performed in the absence of any histatin peptide inhibitor. The activity is monitored continuously at 405 nm using a Molecular Devices $V_{max}$ microtitre plate reader. The activities are determined from the maximum rates of substrate hydrolysis. Assays are done in duplicate, and the means normalized to the controls.

What is claimed is:

1. A substantially pure peptide containing between 13 and 20 amino acids, inclusive, wherein the peptide has the amino acid sequence:

R1-R2-R3-R4-R5-R6-R7-R8-R9-R10-R11-R12-R13-R14-R15-R16-R17-R18-R19-R20-R21-R22-R23 wherein
 R1 is Asp or is absent;
 R2 is Ser or is absent;
 R3 is His or is absent;
 R4 is Ala;
 R5 is Lys, Gln, Arg, or another basic amino acid;
 R6 is Arg, Gln, Lys, or another basic amino acid;
 R7 is His, Phe, Tyr, Leu, or another hydrophobic amino acid;
 R8 is His, Phe, Tyr, Leu, or another hydrophobic amino acid;
 R9 is Gly, Lys, Arg, or another basic amino acid;
 R10 is Tyr;
 R11 is Lys, His, Phe, or another hydrophobic amino acid;
 R12 is Arg, Gln, Lys, or another basic amino acid;
 R13 is Lys, Gln, Arg, another basic amino acid, or is absent;
 R14 is Phe or is absent;
 R15 is His, Phe, Tyr, Leu, another hydrophobic amino acid, or is absent;
 R16 is Glu or is absent;
 R17 is Lys or is absent;
 R18 is His or is absent;
 R19 is His or is absent;
 R20 is Ser or is absent;
 R21 is His or is absent;
 R22 is Arg or is absent;
 R23 is Gly or is absent;
wherein Gln cannot simultaneously occupy positions R5, R6, R12, and R13 of the amino acid sequence, and wherein when R5, R6, R7, R8, R9, R12, R13 and R15 simultaneously are Lys, Arg, His, His, Gly, Arg, Lys and His, respectively, then R11 is His, Phe or another hydrophobic amino acid other than Lys.

2. The peptide of claim 1, wherein at least one of R7, R8, R11, and R15 is Phe.
3. The peptide of claim 1, wherein R7 is Phe.
4. The peptide of claim 1, wherein R8 is Phe.
5. The peptide of claim 1, wherein R11 is Phe.
6. The peptide of claim 1, wherein R15 is Phe.
7. The peptide of claim 1, wherein R7, R8, and R15 are Phe.
8. The peptide of claim 1, wherein R9 is Lys.
9. The peptide of claim 1, wherein R11 is His.
10. The peptide of claim 1, wherein R9 is Lys and R11 is His.
11. The peptide of claim 1, wherein at least one of R7, R8, and R15 is Tyr.
12. The peptide of claim 1, wherein R7, R8, and R15 are Tyr.
13. The peptide of claim 1, wherein R1, R2, and R3 are absent.
14. The peptide of claim 1, wherein R22 and R23 are absent.
15. The peptide of claim 1, wherein R20, R21, R22, and R23 are absent.
16. The peptide of claim 1, wherein R18, R19, R20, R21, R22, and R23 are absent.
17. The peptide of claim 1, wherein the peptide has at least one modification selected from the group consisting of
 (a) an acetyl or a carbamyl addition at the N-terminus; and
 (b) an amide addition at the C-terminus.
18. A pharmaceutical composition comprising a substantially pure peptide containing between 13 and 20 amino acids, inclusive, wherein the peptide has the amino acid sequence:

R1-R2-R3-R4-R5-R6-R7-R8-R9-R10-R11-R12-R13-R14-R15-R16-R17-R18-R19-R20-R21-R22-R23 wherein
 R1 is Asp or is absent;
 R2 is Ser or is absent;
 R3 is His or is absent;
 R4 is Ala;
 R5 is Lys, Gln, Arg, or another basic amino acid;
 R6 is Arg, Gln, Lys, or another basic amino acid;
 R7 is His, Phe, Tyr, Leu, or another hydrophobic amino acid;
 R8 is His, Phe, Tyr, Leu, or another hydrophobic amino acid;
 R9 is Gly, Lys, Arg, or another basic amino acid;
 R10 is Tyr;
 R11 is Lys, His, Phe, or another hydrophobic amino acid;
 R12 is Arg, Gln, Lys, or another basic amino acid;
 R13 is Lys, Gln, Arg, another basic amino acid, or is absent;
 R14 is Phe or is absent;
 R15 is His, Phe, Tyr, Leu, another hydrophobic amino acid, or is absent;
 R16 is Glu or is absent;
 R17 is Lys or is absent;
 R18 is His or is absent;

R19 is His or is absent;
R20 is Ser or is absent;
R21 is His or is absent;
R22 is Arg or is absent;
R23 is Gly or is absent;
wherein Gln cannot simultaneously occupy positions R5, R6, R12, and R13 of the amino acid sequence.

19. The composition of claim 18, wherein at least one of R7, R8, R11, and R15 is Phe.

20. The composition of claim 18, wherein R7, R8, and R15 are Phe.

21. The composition of claim 18, wherein R9 is Lys and R11 is His.

22. The composition of claim 18, wherein R7, R8, and R15 are Tyr.

23. The composition of claim 18, wherein the peptide has at least one modification selected from the group consisting of
   (a) an acetyl or a carbamyl addition at the N-terminus; and
   (b) an amide addition at the C-terminus.

24. A method for treating a fuingal or bacterial infection in a mammal, the method comprising administering to the mammal a therapeutically effective amount of a peptide containing between 13 and 20 amino acids, inclusive, wherein the peptide has the amino acid sequence:

R1-R2-R3-R4-R5-R6-R7-R8-R9-R10-R11-R12-R13-R14-R15-R16-R17-R18-R19-R20-R21-R22-R23 wherein
   R1 is Asp or is absent;
   R2 is Ser or is absent;
   R3 is His or is absent;
   R4 is Ala;
   R5 is Lys, Gln, Arg, or another basic amino acid;
   R6 is Arg, Gln, Lys, or another basic amino acid;
   R7 is His, Phe, Tyr, Leu, or another hydrophobic amino acid;
   R8 is His, Phe, Tyr, Leu, or another hydrophobic amino acid;
   R9 is Gly, Lys, Arg, or another basic amino acid;
   R10 is Tyr;
   R11 is Lys, His, Phe, or another hydrophobic amino acid;
   R12 is Arg, Gln, Lys, or another basic amino acid;
   R13 is Lys, Gln, Arg, another basic amino acid, or is absent;
   R14 is Phe or is absent;
   R15 is His, Phe, Tyr, Leu, another hydrophobic amino acid, or is absent;
   R16 is Glu or is absent;
   R17 is Lys or is absent;
   R18 is His or is absent;
   R19 is His or is absent;
   R20 is Ser or is absent;
   R21 is His or is absent;
   R22 is Arg or is absent;
   R23 is Gly or is absent;
wherein Gln cannot simultaneously occupy positions R5, R6, R12, and R13 of the amino acid sequence.

25. The method of claim 24, wherein at least one of R7, R8, R11, and R15 is Phe.

26. The method of claim 24, wherein R7, R8, and R15 are Phe.

27. The method of claim 24, wherein R9 is Lys and R11 is His.

28. The method of claim 24, wherein R7, R8, and R15 are Tyr.

29. The method of claim 24, wherein the peptide has at least one modification selected from the group consisting of
   (a) an acetyl or a carbamyl addition at the N-terminus; and
   (b) an amide addition at the C-terminus.

* * * * *